United States Patent
Kankkunen

[11] Patent Number: 6,138,672
[45] Date of Patent: Oct. 31, 2000

[54] ARRANGEMENT IN ANESTHESIA VAPORIZER

[75] Inventor: Jukka Kankkunen, Helsinki, Finland

[73] Assignee: Instrumentarium Corp., Helsinki, Finland

[21] Appl. No.: 09/063,598

[22] Filed: Apr. 21, 1998

[30] Foreign Application Priority Data

May 2, 1997 [FI] Finland ..................... 971898

[51] Int. Cl.$^7$ .................. A61M 15/00
[52] U.S. Cl. .............. 128/203.12; 128/203.16; 128/200.11; 141/2; 141/18; 141/46
[58] Field of Search ............ 128/202.27, 203.12, 128/203.13, 203.14, 200.11, 203.16, 203.26, 204.13, 204.14; 141/2, 4, 5, 18, 21, 44, 46

[56] References Cited

U.S. PATENT DOCUMENTS

| | | |
|---|---|---|
| 3,536,108 | 10/1970 | Schreiber . |
| 4,454,893 | 6/1984 | Orchard . |
| 4,715,370 | 12/1987 | Altner et al. ............ 128/203.12 |
| 5,419,316 | 5/1995 | Bernstein ............... 128/203.12 |
| 5,427,145 | 6/1995 | Grabenkort et al. ....... 128/203.13 |
| 5,470,511 | 11/1995 | Laybourne et al. ........ 128/203.12 |
| 5,505,236 | 4/1996 | Grabenkort et al. ....... 128/203.12 |
| 5,509,405 | 4/1996 | Mashak ................. 128/203.12 |

FOREIGN PATENT DOCUMENTS

| | | |
|---|---|---|
| 467068 | 1/1992 | European Pat. Off. . |
| 41 06 906 | 9/1992 | Germany . |
| 95/15778 | 6/1995 | WIPO . |

*Primary Examiner*—John G. Weiss
*Assistant Examiner*—V. Srivastava
*Attorney, Agent, or Firm*—Andrus, Sceales, Starke & Sawall, LLP

[57] ABSTRACT

An arrangement in an anesthesia vaporizer comprising a liquid container including a vapor generator; a filling device; and conduits for supplying anesthetic from a transport and storage container to the liquid container and/or for removing anesthetic from the liquid container, and for conveying an amount of replenishment gas corresponding to the amount of anesthetic liquid from the liquid container to the transport and storage container upon filling the container and/or inversely upon emptying. For improved operating safety, the filling device is provided with a closing means, adapted to close a filling conduit which opens to the inside of the liquid container and a replenishment gas conduit between the liquid container and the transport and storage container through an overpressure generated in the transport and storage container, and thus prevent anesthetic liquid from flowing to the liquid container.

14 Claims, 2 Drawing Sheets

006,138,672

ARRANGEMENT IN ANESTHESIA VAPORIZER

BACKGROUND OF THE INVENTION

The invention relates to an arrangement in an anesthesia vaporizer comprising a liquid container including a vapor generator; a filling device; and conduits for supplying anesthetic from a transport and storage container to the liquid container and/or for removing anesthetic from the liquid container, and for conveying an amount of replenishment gas corresponding to the amount of anesthetic liquid from the liquid container to the transport and storage container upon filling the container and/or reversely upon emptying.

Anesthesia devices are used e.g. during operations in operating theaters in hospitals. The most essential components of an anesthesia device are a vaporizer and a dosing device for anesthetic. These components may be integrated or separate, as in cassette-type structures. The main components of a vaporizer are a liquid container including a vapor generator, and a filling device. The filling device serves to supply and remove anesthetic from the liquid container. Anesthetic liquids are stored in transport and storage containers, or flasks, each anesthetic liquid having a dedicated profile-coded flask opening. A flask can be connected only to a filling device suitable for each particular anesthetic either directly or through a profile-coded adapter.

Unlike other anesthetics, a currently used anesthetic liquid boils in room temperature, whereby the pressure inside the flask rises as the temperature rises. This anesthetic liquid is desflurane. This is one of the reasons why the opening of a desflurane anesthetic flask is provided with a profile-coded valve part. When the flask opening is inserted into the counterpart of the filling device, a tight filling conduit is provided between the flask and the valve of the filling device, and on inserting the flask opening deeper, the valves of the flask and the filling device are opened, the structure of the filling device determining the opening order, the number of valves, filling motions etc. If, owing to an increase in the temperature, the pressure in the flask containing desflurane anesthetic rises to a high level, this can result in an overfilled liquid container. In the worst case, anesthetic may flow from an overfilled liquid container to the dosing device, causing e.g. malfunction in the entire anesthesia device.

BRIEF SUMMARY OF THE INVENTION

It is the object of the invention to provide an arrangement by means of which the prior art drawbacks can be eliminated. In other words, the object is to provide an arrangement by which the container cannot be filled or the filling is very slow if the pressure difference between the flask and the container is great. This is achieved by means of the arrangement of the invention, characterized in that the filling device is provided with a closing means, adapted to close a filling conduit which opens to the inside of the liquid container and a replenishment gas conduit between the liquid container and the transport and storage container through overpressure generated in the transport and storage container, and thus to prevent anesthetic liquid from flowing to the liquid container.

The main advantage of the invention is its simplicity, making the implementation and use of the invention advantageous. Owing to the simplicity, the arrangement of the invention also operates reliably. The arrangement of the invention also operates very efficiently, i.e. under certain circumstances the arrangement closes the filling conduit very efficiently, resulting in a still improved total safety in anesthesia.

BRIEF DESCRIPTION OF THE SEVERAL VIEWS OF THE DRAWINGS

In the following the invention will be described in greater detail by means of the preferred embodiments described in the attached drawings, in which.

DETAILED DESCRIPTION OF THE INVENTION

Figure 1:
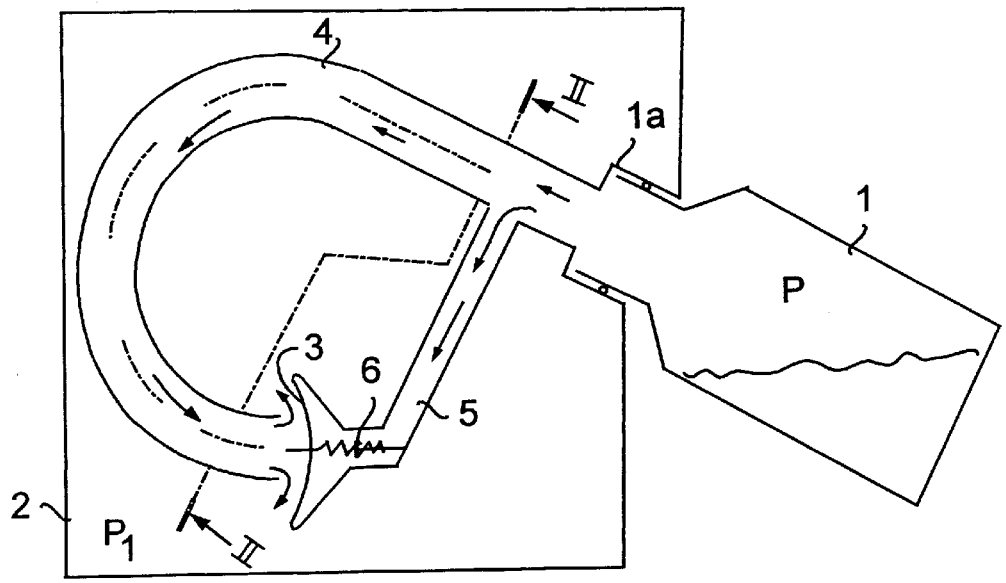
FIG. 1 is a schematic view of the arrangement of the invention in a normal filling situation.
Figure 2:
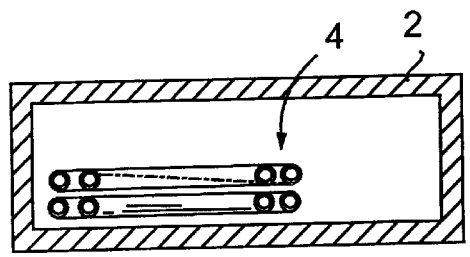
FIG. 2 is a cross-sectional view of a detail of the arrangement of FIG. 1 along arrows II—II.
Figure 3:
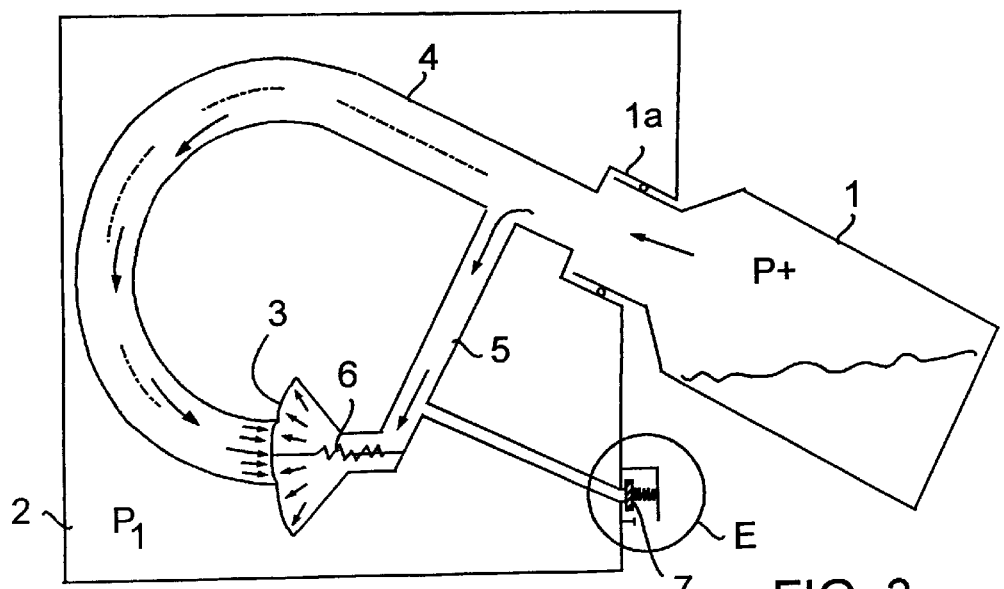
FIG. 3 is a schematic view of the arrangement of the invention in an overpressure situation.

FIGS. 1 to 3 show a schematic simplified form of the arrangement of the invention. FIG. 1 shows the arrangement of the invention in a normal filling situation, i.e. a situation where the difference between a pressure P of a transport and storage container 1, or flask, and a pressure $P_1$ of a liquid container 2 is very small. In FIG. 1, the flask 1 is placed tightly to a filling device 1a. In this situation the pressure of the flask 1 is allowed to be discharged to the container 2 causing only a small pressure shock to a closing means 3, 5. When the flask is lifted, the liquid is allowed to flow along a filling conduit 4 to the container. The filling conduit 4 can be formed of a plurality of pipes with a small diameter as is shown in FIG. 2. It should be noted that this is a closed system, i.e. if liquid flows from the flask to the container, a corresponding amount of replenishment gas has to be conveyed from the container to the flask. In other words, a flow conduit has to be provided for the replenishment gas. In the case of FIG. 2, some pipes also serve as a flow conduit for replenishment gas.

In the implementation of FIG. 1, the closing valve 3 is disposed in the closing conduit 5 whose volume is smaller than that of the filling conduit 4. It must be noted that the filling conduit 4 is considered to start from the juncture of the closing conduit 5. The length of the closing conduit may naturally vary. The closing valve 3 is in the vicinity of the outlet of the filling conduit in FIGS. 1 to 3, faces it in the example of FIGS. 1 and 3, the closing valve being opposite the outlet of the filling conduit 4 at a small distance from it. In FIG. 1 the closing valve is in a non-pressurized initial position, i.e. a position in which the outlet of the flow conduit 4 and the flow opening in the replenishment gas container 2 are open. It is to be noted that said conduits and flow openings can be the same as has been specified above.

FIG. 3 shows the arrangement of FIG. 1 in a situation where the difference between the pressure P+ in the flask 1 and the pressure $P_1$ in the container 2 is great. In this situation the pressure of the flask is allowed to be discharged into the filling conduit 4 and the closing conduit 5. When the volume of the closing conduit 5 is smaller than the volume of the filling 4, the pressure shock reaches the side of the closing valve 3 facing the closing conduit 5 earlier than the side facing the filling conduit 4, the closing valve 3 moving from said initial position to a position closing the filling conduit 4. In other words, the closing valve 3 closes the end of the filling conduit by pressing against the end of the filling conduit as is shown in FIG. 3. In this situation, when the flask 1 is being turned, the liquid cannot flow to the container 2. In this position the closing valve 3 also closes the replenishment gas conduit thereby ensuring that the liquid cannot flow to the container through said conduit owing to overpressure. In the implementation of FIGS. 1 to 3, a flow resistance is further arranged to the filling conduit 4 behind the branching point of the closing conduit 5. Said flow resistance is provided by forming the filling conduit 4 with a plurality of pipes having a small diameter, the pipes causing the flow to throttle. It is obvious that the flow resistance can also be provided by arranging a throttle point to the conduit by narrowing the conduit etc. The flow resistance ensures that overpressure is discharged through the closing means 3, 5 in the above described manner.

The closed filling conduit 4 opens when filling is restarted by using a flask that is cold or at room temperature, since the overpressure in the conduit is allowed to get stabilized into a cool flask. In other words, when pressure falls, the closing valve 3 is arranged to return to the initial position from the position which closes the filling conduit 4. At the same time the replenishment gas conduit naturally also opens. The opening of the closing valve 3 can be sped up e.g. by designing the valve that closes the conduit such that there is no absolute tightening but instead a small leakage, and a return spring 6 and/or some other similar mechanism open the conduit automatically.

Figure 4:
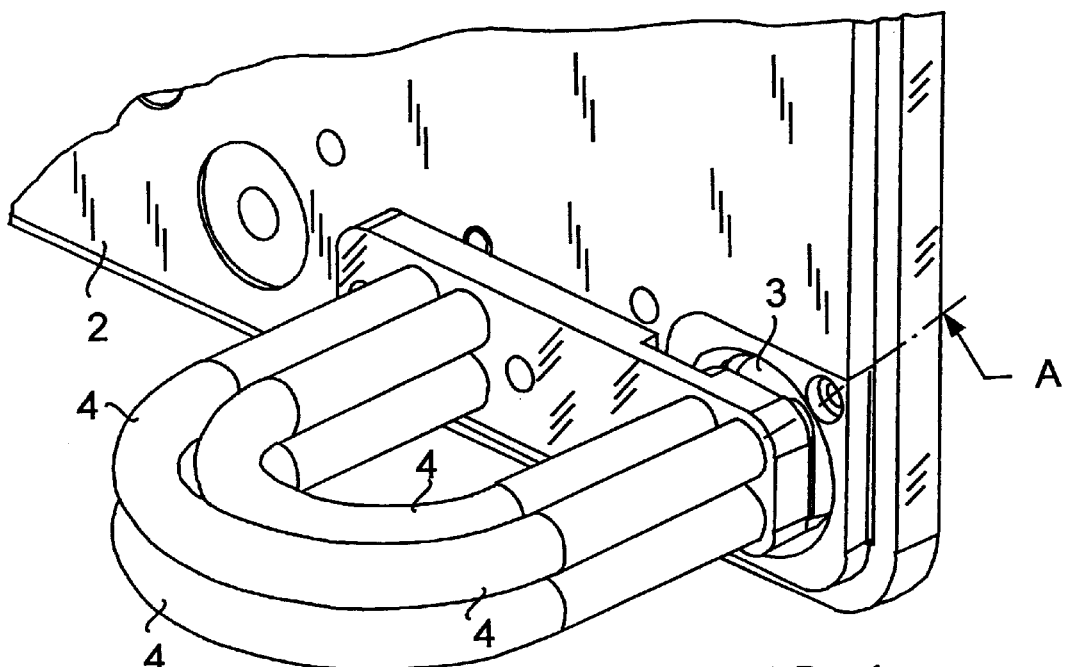
FIG. 4 shows an example of how the arrangement of the invention is placed in a vaporizer.
Figure 5:
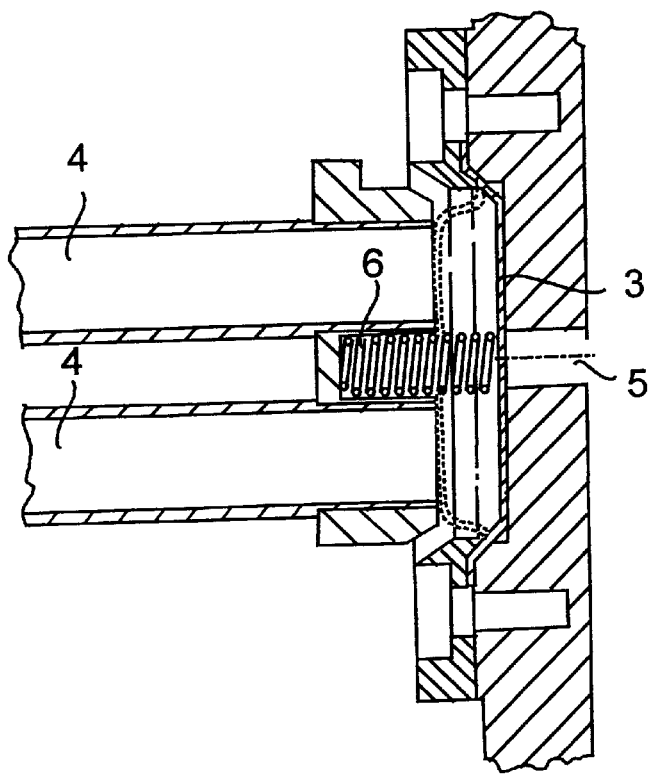
FIG. 5 is a cross-sectional view of the arrangement of the implementation of FIG. 4 in accordance with arrow A.

A simple closing valve is achieved e.g. by the solution of FIGS. 4 and 5. In FIGS. 4 and 5 the same reference numerals are used for points corresponding to those in FIGS. 1 to 3. FIGS. 4 and 5 show an application in which the closing valve is placed at the end of an arched filling pipe structure that prevents overfilling and a wrong filling position. However, it is obvious that the closing valve can also be placed into a filling system that lacks said safety solution. FIG. 4 shows only one wall of the container 2 for the sake of clarity. However, it is obvious that in an actual device the filling pipe structure of FIG. 4 is placed inside the container 2 according to the principle shown in FIGS. 1 to 3.

In the example of FIGS. 4 and 5 the closing valve is formed of an elastic membrane part 3 serving as the actual closing part and of the return spring 6. It is obvious that the membrane part 3 can also be formed such that the membrane part itself also operates as the return spring. In FIG. 5, the membrane part 3 is shown in an initial position, i.e. in a position corresponding to the situation in FIG. 1. However, FIG. 4 also shows with dashed lines the membrane part in a position where it shuts the filling conduit. Thus, the position of the membrane part 3 shown with dashed lines corresponds to the situation of FIG. 3. It is advantageous to dimension the closing valve such that its area on which the pressure is acting on the side where overpressure is effective, i.e. in the examples of the figures on the side of the closing conduit 5, is larger than the area on which the pressure is acting on the side of the filling conduit 4. The closing valve can also be a structure based on a metal membrane or glass, or e.g. a piston type structure.

The excessive pressures in the container 2 can cause harm to the device and to the patient. It is therefore advantageous to arrange a relief valve in association with the closing means 3, 5. In FIG. 3, reference E shows the point where a relief valve 7 is arranged. In FIG. 2 the relief valve is placed in flow communication with the closing conduit 5, but it is obvious that the relief valve can also be placed somewhere else, e.g. in association with the closing valve. Hazardous pressures are discharged by means of the relief valve 7 to the outside of the device. The opening pressure of the relief valve 7 can naturally be arranged according to the need. The type of the relief valve 7 can be any known solution.

In the foregoing the invention has been described in greater detail by means of an embodiment utilizing a closing conduit. The closing conduit 5 is in flow communication substantially only with the space which is able to transfer the pressure of the flask 1 to the closing valve 3. In this case the closing conduit is preferably connected to the filling conduit 4 or to a point which can be upstream from the filling conduit all the way to the flask 1. Utilizing a closing conduit is, however, not the only choice, but the invention may also be applied by forming the closing means using a closing valve. Such an application can be described as follows. As has been stated above, the length of the closing conduit may vary. When studying the example of FIGS. 1 to 3, it is feasible that the length of the closing conduit 5 is decreased, the limit being a solution in which the length of the closing conduit 5 is zero. In other words a solution in which the closing valve 3 is placed into the branching point of the closing channel shown in FIGS. 1 and 3. Naturally, the outlet of the filling conduit 4 has to be placed similarly such that it is located close to the closing valve 3 in accordance with the basic principle shown in FIGS. 1 and 3. The outlet can be placed in the above described manner by extending the filling pipe such that the outlet is disposed close to the branching point of the closing conduit shown in FIGS. 1 and 3. In this embodiment the closing valve 3 operates in the same way as in the above described examples.

The above described examples of the embodiments are in no way intended to restrict the invention, but the invention may be freely modified within the scope of the claims. Thus it is obvious that the inventive arrangement or its parts do not necessarily have to be similar to those presented in the figures, but other solutions are possible, too. For example the part of the closing valve which is subjected to overpressure may also be a part different from the part closing the flow conduit. A connection has to be provided between said parts. Said parts can be formed of e.g. piston elements and a mechanical connection be provided between them. The connection may also be electrical. The closing means may also be provided by the overpressure affecting a sensor which in turn controls a means closing the filling conduit. The sensor can naturally be adjusted to issue a closing command after a given exceeding of the pressure limit etc.

What is claimed is:

1. A filling system including an anesthetic storage container and an anesthetic vaporizer having a liquid container, the filing system for use in transferring an anesthetic between the anesthetic storage container and the liquid container within the anesthetic vaporizer, the filling system comprising:

a filling device positioned on the anesthetic vaporizer to receive the anesthetic storage container;

at least one filling conduit having a first end including a flow opening in communication with the liquid container of the anesthetic vaporizer and a second end coupled to the filling device, the filling conduit providing a pathway for both the anesthetic from the anesthetic storage container and a replenishment gas to flow between the anesthetic storage container and the liquid container of the anesthetic vaporizer; and closing means operatively positioned adjacent to the flow opening of the filling conduit, the closing means being movable to a closing position when a first pressure in the anesthetic storage container substantially exceeds a second pressure in the liquid container of the anesthetic vaporizer, whereby when the closing means is in the closing position, the closing means closes the flow opening of the filling conduit to prevent anesthetic liquid from flowing from the anesthetic storage container into the liquid container of the anesthetic vaporizer.

2. The filling system of 1 wherein the closing means includes a closing valve positioned adjacent to the flow opening of the replenishment gas conduit within the liquid container, the closing valve being moved to a closed position by the first pressure discharged from the anesthetic storage container, wherein when the closing valve is in the closed position, the closing valve closes the flow opening to the filling conduit.

3. The filling system of claim 2 wherein the closing means further includes a closing conduit extending between a first end and a second end, the first end of the closing conduit being coupled to the filling conduit at a branching point, the second end of the filling conduit including the closing valve, wherein the closing conduit has a volume smaller than the volume of the filling conduit.

4. The filling system of claim 3 wherein a flow resistance is disposed in the filling conduit between the branching point and the first end of the filling conduit.

5. The filling system of claim 2 wherein as the first pressure within the anesthetic storage container decreases relative to the second pressure in the liquid container of the anesthetic vaporizer, the closing valve is arranged to return to an initial position in which the filling conduit is open.

6. The filling system of claim 5 wherein the closing valve is dimensioned such that the surface area on the side where first pressure from the anesthetic storage container is effective is larger than the surface area on the side facing the filling conduit.

7. The filling system of claim 2 herein the closing valve is placed in association with a safety mechanism arranged at the end of the filling conduit for preventing overfilling and a wrong filling position.

8. The filling system of claim 1 wherein a relief valve is arranged in association with the closing means to discharge an overpressure that is hazardous to a patient.

9. The filling system of claim 8 wherein the relief valve is arranged to be in flow communication with a closing conduit extending between the filling device and the closing means.

10. The filling system arrangement of claim 1 wherein the closing means is arranged inside the vaporizer.

11. A filling system including an anesthetic storage container and an anesthetic vaporizer having a liquid container, the filing system for use in transferring an anesthetic between the anesthetic storage container and the liquid container within the anesthetic vaporizer, the filling system comprising:

a filling device positioned on the anesthetic vaporizer to receive the anesthetic storage container;

at least one replenishment gas conduit having a first end including a flow opening in pressure communication with the liquid container of the anesthetic vaporizer and a second end coupled to the filling device, the replenishment gas conduit providing a gas flow passageway between the anesthetic storage container and the liquid container of the anesthetic vaporizer when the anesthetic storage container is received within the filling device;

at least one filling conduit having a first end including a flow opening in communication with the liquid container of the anesthetic vaporizer and a second end coupled to the filling device, the filling conduit providing a fluid passageway between the anesthetic storage container and the liquid container of the anesthetic vaporizer when the anesthetic storage container is received within the filling device;

a closing conduit having a first end in pressure communication with the anesthetic storage container at a branching point near the filling device, the closing conduit having a second end positioned in the liquid container of the anesthetic vaporizer; and a closing valve connected to the second end of the closing conduit, the closing valve being positioned adjacent to the flow openings of both the replenishment gas conduit and the filling conduit, wherein the closing valve moves to a closed position to close the flow openings of both the replenishment gas conduit and the filling conduit when a first pressure within the anesthetic storage container substantially exceeds a second pressure within the liquid container, thereby preventing anesthetic liquid from flowing into the liquid container from the anesthetic storage container upon an overpressure in the anesthetic storage container.

12. The filling system of claim 11 wherein a relief valve is in communication with the closing conduit to discharge the overpressure within the anesthetic storage container.

13. The filling system of claim 11 wherein the volume of the closing conduit is less than the volume of the filling conduit such that the pressure difference between the anesthetic storage container and the liquid container causes the closing valve to close prior to anesthetic being transferred from the anesthetic storage container to the liquid container.

14. The filling arrangement of claim 11 herein the first end of the closing conduit is coupled to the filling conduit at the branching point near the filling device.

* * * * *